United States Patent [19]

Flinchbaugh

[11] Patent Number: 4,865,588
[45] Date of Patent: Sep. 12, 1989

[54] MAGNETIC BLADDER CYCLER AND USE METHOD

[75] Inventor: David E. Flinchbaugh, Orlando, Fla.

[73] Assignee: Medical Inventor's Corp., Orlando, Fla.

[21] Appl. No.: 238,484

[22] Filed: Aug. 31, 1988

[51] Int. Cl.⁴ .................................................. A61M 27/00
[52] U.S. Cl. ........................... 604/129; 128/DIG. 25; 251/65; 604/10; 604/247
[58] Field of Search ................................ 604/8–10, 604/247, 118, 129; 128/DIG. 25; 600/29, 30; 251/65

[56] References Cited

U.S. PATENT DOCUMENTS

| | | | |
|---|---|---|---|
| 2,667,895 | 2/1954 | Pool et al. | 251/65 X |
| 3,105,511 | 10/1963 | Murphy | 251/65 X |
| 3,495,620 | 2/1970 | Raimondi et al. | 251/65 X |
| 3,731,670 | 5/1973 | Loe | 128/DIG. 25 |
| 3,758,073 | 9/1973 | Schulte | 604/9 X |
| 4,424,058 | 1/1984 | Parsons et al. | 604/247 X |
| 4,705,070 | 11/1987 | Eidsmore | 251/65 X |

Primary Examiner—Dalton L. Truluck

[57] ABSTRACT

A bladder cycler is provided with a magnetic valve for hospital, nursing home, and home care use in automatic emptying of the bladder of a patient. Manual override also is provided with variable opening pressure.

50 Claims, 1 Drawing Sheet

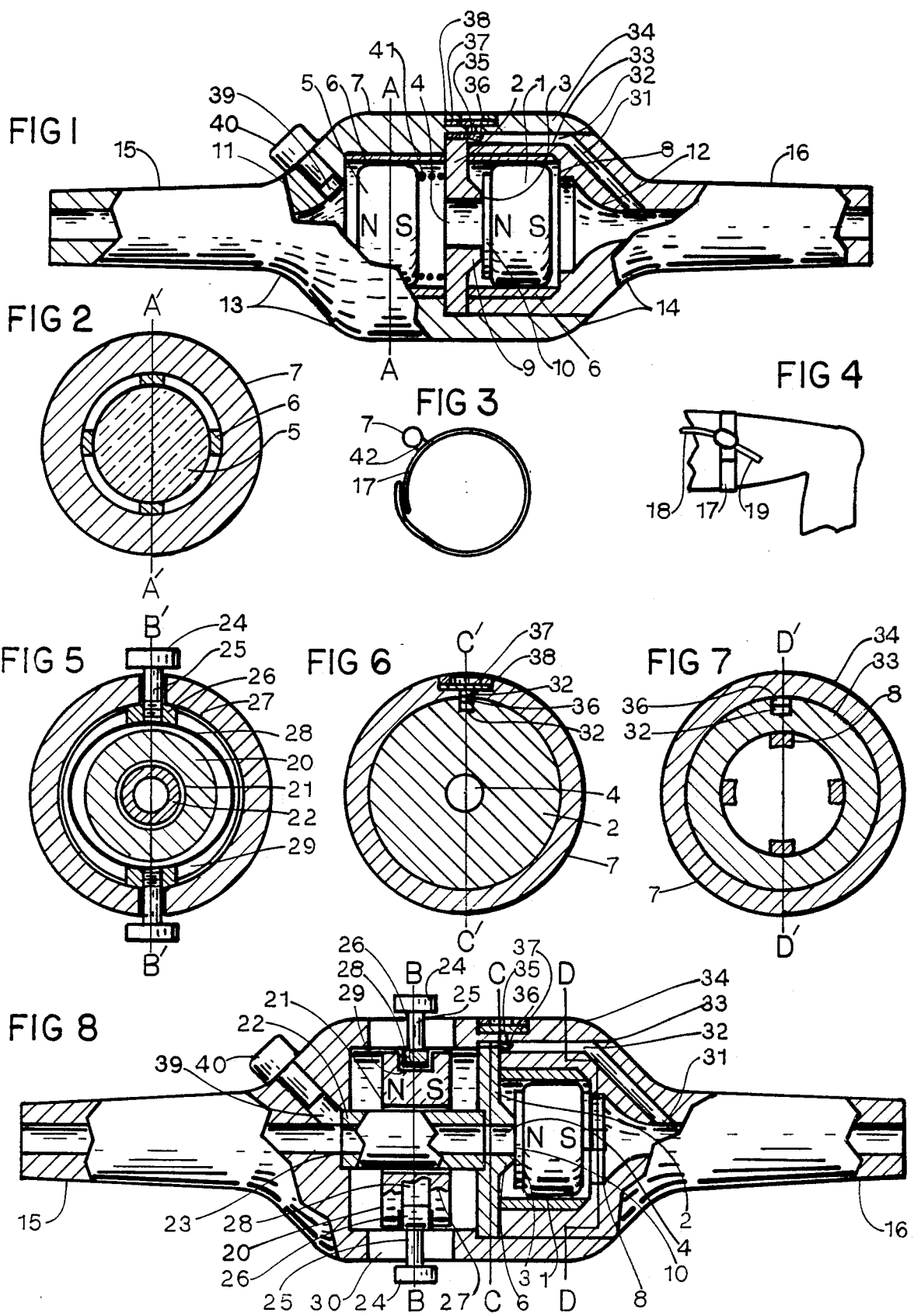

MAGNETIC BLADDER CYCLER AND USE METHOD

BACKGROUND OF THE INVENTION

1. Technical Field.

This invention relates to a bladder drainage cycler and method of use. It is a hospital instrument for draining urine from bladders of patients automatically, thoroughly and antiseptically when necessary to bypass natural bladder drainage.

2. Background Information

Hospital instruments and procedures for draining bladders of patients has evolved from constant uncycled drainage through siphoning, suction and various types of cyclic methods. Fundamental to an effective instrument and method is allowing the bladder to fill reasonably and then draining it without a suction effect and without allowing build-up or entry of infectious contaminants in the drainage system.

Included in previous methods have been U.S. Pat. Nos. 2,602,448 and 2,860,636 which utilized a siphon in combination with a reservoir to provide cycle draining of the bladder. Pressure release in these is controlled by raising the height of the device on a bedside tree. It is subject to distortion by shifting and turning of the patient and therefore, very undependable in addition to being restrictive of the patient.

In U.S. Pat. No. 3,598,124, a siphon leg is controlled by merely attaching a catheter to a bedside tree at predetermined adjusted height, which varies the pressure at which the bladder will drain and provides a flutter valve near the patient to break the siphon action of the system once the bladder has drained. In U.S. Pat. No. 4,230,102, a device for the draining of a bladder is shown in which a T-joint has been placed on a catheter and has a pressure membrane attached thereto in a large casing for actuating a pressure switch which in turn actuates an electric motor driving a gear train and cam. A cam follower is spring loaded to clam the catheter for two minute cycles upon actuation by the pressure switch to drain the bladder. This type of device, however, is expensive and bulky and positions an electrical apparatus adjacent to the catheter. In U.S. Pat. No. 4,424,058, a spring-return valve is provided in conjunction with a siphon-release orifice to prevent excessive suction and to prevent urine from remaining in the system after drainage. A problem with this system was that resiliency of the spring increased with distance of travel from a closed position. This tended to cause some fluid to remain in the bladder because only a full bladder would open it and only a relatively full bladder would keep it open to allow complete drainage unless overridden by the patient. Also, positioning of tubes leading from it were parallel to the leg on which it was attached and provided a situation for retention of fluid in the system.

This invention provides magnetic closing of a valve member with decreased rather than increased closing pressure when opened. As the bladder is emptied, decreasing head pressure against the valve, therefore, can keep the valve open for more complete drainage than can be provided by a resiliency-operated valve.

Valve-closing pressure decreases as a result of three factors: (1) magnetic pull of a valve decreases as its open distance from magnetic attraction in the direction of a valve seat increases, (2) fluid passing through the system provides a partial insulation which tends to decrease magnetic attraction between magnetic members, and (3) an optional spring in one of the embodiments of the invention causes the magnetic members to be further apart when the valve opens. In addition, one of the embodiments of the invention provides convenient manual override to decrease or eliminate totally the magnetic closing pressure of the valve.

SUMMARY OF THE INVENTION

A bladder drainage wafer valve member is magnetically attracted towards a valve-port wall. Head pressure of urine in a bladder and in a drainage tube from the bladder to the valve where it is positioned on a patient's leg causes the valve to open away from the valve-port wall. When the valve is opened, distance increases between the valve member and a member to which it is magnetically attracted in the direction of the valve-port wall. An optional spring moves the member to which it is attracted yet further away and further decreases the magnetic attraction, thereby allowing the valve to remain open with less pressure than required to open it. Fluid passing between the open valve and the member to which it is attracted magnetically decreases further yet the closing pressure to offset the head-pressure opening of the valve.

Downstream from the valve, there is a siphon-release air-inlet orifice that relieves siphon pressure to avoid siphon suction that would either cause collapse of the bladder walls or cause the valve to remain open after the bladder is emptied. An air inlet to the siphon-release orifice is positioned upstream and radially outward from an outlet to the valve in order to prevent passage of fluid from the valve where siphon pressure does not provide sufficient inward suction of air. The siphon-release orifice is provided with an antiseptic strainer and a low-pressure one-way inlet valve.

Optionl embodiments of this invention provide manual override of the valve by selective distancing of a magnetic member from the valve member that is attracted to it. This gives flexibility of pressure adjustment and provides the opportunity of assuring full drainage when desired.

A swivelable attachment of the bladder cycler to a strap on a patient's leg allows it to be positioned at a slant with he outlet and tubes leading from it downward from the valve to further assure that fluid will not remain in the system between drainage cycles whether used in either a prone or vertical position of the leg.

BRIEF DESCRIPTION OF THE DRAWINGS

The objects, features and advantages of this invention will be apparent from the written description of the drawings in which:

FIG. 1 is a cutaway side view of a fully automatic drainage embodiment of this invention;

FIG. 2 is a cross-section view through position AA FIG. 1;

FIG. 3 is an end view of a medical leg strap with a swivelable attachment of a magnetic cycler;

FIG. 4 is a side view of the invention strapped in slanting position on a patient's leg. slanting FIG. 5 is a cross-section view through position BB of a manual override form of the invention shown in FIG. 8;

FIG. 6 is a cross-section view through position CC of the manual override form of the invention shown in FIG. 8;

FIG. 7 is a cross-section view through position DD of the manual override form of the invention shown in FIG. 8; and FIG. 8 is a cutaway side view of a manual override embodiment of this invention.

DESCRIPTION OF PREFERRED EMBODIMENTS

Referring to FIG. 1, a magnetic valve member 1 is magnetically attracted in the direction of valve-port wall 2 having valve seat 3 at an outlet end of valve orifice 4. The magnetic valve member can be attracted magnetically to either the valve-port wall or to an upstream magnetic member 5. Magnetic attraction can be provided by construction of either or both the valve member and the upstream magnetic member. Optionally and preferably, the magnetic valve member and the upstream magnetic member both magnetic force and the valve-port wall is non-magnetic. When either the valve-port wall or the magnetic base member have magnetic force and the magnetic valve member also has magnetic force, opposite poles of each are facing each other.

Referring to FIGS. 1, and 2, channel ridges 6 at the inside periphery of non-magnetic housing 7 provide fluid passage linearly between them from side-to-side of first the magnetic base member and then the magnetic valve member.

Referring to FIG. 7, stopper shoulders 8 are provided to arrest travel of the magnetic valve member at a select distance of travel from the valve-port wall. Referring to FIGS. 1 and 8, the valve-port wall is provided with an optional valve-seat ridge 9 for reduction of valve-seat area to reduce area for accumulation of particulates in fluid passing through the system and for providing a relatively sharp surface for tightly seating into the valve member. A resilient non-magnetic valve surface 10 can be provided for increased seating pressure and for selectively decreased magnetic attraction in the direction of the valve-port wall.

Referring to FIGS. 1 and 8, inside corners of magnetic valve inside corners of housing inlets 11, inside corners of housing outlets 12 and all other corners possible can be rounded to facilitate flow through the system and to prevent accumulation of particulates in fluid passing through the system. Outside inlet corners 13 and outlet corners 14 also can be rounded to prevent scraping action that would tend to accumulate particles at the outside and decrease cleanliness. In addition to being rounded, the inside corners of the housing outlets are shaped at an angle from the inlet connectors 15 and the outlet connectors 16 which can be selectively tapered to receive and to hold medical tubing.

Referring to FIGS. 3 and 4, a leg strap 17 is provided with a swivel connection 42 that allows the bladder cycler to be positioned when desired at a downward angle with respect to a leg to which it attached. This allows drainage tubing 18 and outlet tubing 19 to be positioned at a slant that provides downward flow of all fluid that otherwise could remain in the system between drainage cycles.

Referring to FIG. 8, the magnetic valve members can be the same as illustrated for the embodiment in FIG. 1 and, therefore, are numbered the same from position CC at the valve-port wall in a direction downstream towards the housing outlet connectors. Upstream from the valve-port wall, a magnetic base member 20 with inside periphery of a bearing orifice 21 is in slidable contact with the outside periphery of bearing tube 22 which is extended between housing inlet 23 and the valve-port wall.

Referring to FIGS. 5 and 8, at each side of the housing, a control button 24 is provided with a with button stem 25 which is attached to a control traction member 26 at the inside periphery 27 of the housing. The traction members are pressured against the inside periphery by a circular ringshaped traction spring 28. The traction spring and the traction member are both contained in a control channel 29 at the outside periphery of the magnetic base member. The traction member and the spring can be constructed of non-magnetic materials and the spring can be formed of non-metallic resilient material The traction spring is held in an elliptical form by the thickness of the traction members. Outward pressure of the spring tending to become circular can be relieved and thus relieve traction pressure against the inside periphery of the housing when the buttons are both pressured inwardly with fingers of an operator. Requirement of two fingers, one at each side or the cycler, allows the cycler to remain in the same position when so utilized.

Head pressure to open the valve is decreased by pressing the button inwardly and sliding the magnetic base member in the direction of the housing inlet. The valve is totally released without any magnetic pressure to hold the valve shut when the magnetic base is slid to the extreme end of travel of the button stem in stem channels 30. Closing pressure of the valve is increased by sliding the magnetic base member in a downstream direction toward the housing outlet.

The magnetic base member never comes in contact with fluid in the system because there is sealing at both ends of the bearing tube. There is no need, therefore, for rounded edges of the inlet and the magnetic base member in this override embodiment of the invention.

Referring to FIGS. 1, 6 and 8, a siphon orifice 31 at the housing outlet can be extended to a siphon channel 32 at the outside periphery of a downstream housing member 33 that is inserted into an upstream housing extension 34 to form a conveyance to siphon inlet port 35 having one-way inlet valve 36. The inlet port is provided with a strainer 37 that is insertable into strainer aperture 38.

Referring to FIGS. 1 and 8, an insecticide orifice 39 can be provided at the housing inlets with a sealable cover 40. This allows insertion of insecticide into the system and into the bladder as may be advisable from time-to-time.

Referring to FIG. 1, an automatic-control resilient member such as spring 41 can be employed to pressure the upstream magnetic member in the direction of the housing inlet. This causes the upstream magnetic member to travel further from the magnetic valve member when the magnetic valve member travels to an open position as a result of greater distance between the two attracting magnetic forces increases. This decreases the amount of head pressure to keep the valve open when the bladder is being drained and, therefore, provides a more complete draining of the bladder as it empties and has less head pressure to keep the valve open. Magnetic valve operation provides this same effect in contrast to the effect of a spring closing of valves which increases pressure to keep valves open as head pressure to keep them open decreases. In this working relationship, a spring is an optional improvement upon the magnetic method. A spring in this working relationship works in the opposite direction as springs used to close valves in prior-art practices.

What is claimed is:

1. A magnetic bladder cycler comprising:
   a non-magnetic tubular housing;
   a non-magnetic tubular inlet conveyance positioned concentrically to the axis of an inlet end of the tubular housing;
   a non-magnetic tubular outlet conveyance positioned concentrically to the axis of an outlet end of the tubular housing;
   a valve-port wall positioned stationary within the tubular housing between the inlet and outlet ends thereof and having a valve orifice linear to the axis of the tubular housing;
   a magnetic base member rigidly positionable linearly to the inside periphery of the housing between the valve-port wall and the inlet conveyance at a linear distance from the valve-port wall selected in relationship to magnetic attraction of a magnetic valve member and the magnetic base member to each other;
   a magnetic valve member having magnetic attraction to the magnetic base member at the opposite side of the valve-port wall and having an outside periphery greater than the inside periphery of the valve orifice in slidable contact with portions of the inside periphery of the housing and positioned between the valve-port wall and the outlet end of the tubular housing;
   fluid conveyance means in fluid communication from the inlet conveyance to the valve orifice in the non-magnetic valve-port wall;
   fluid conveyance means in fluid communication from the valve orifice in the non-magnetic valve-port wall to the outlet conveyance; and
   a siphon-vent orifice positioned at the outlet end of the tubular housing.

2. A bladder cycler in accordance with claim 1 wherein:
   the magnetic attraction of the valve member to the magnetic base member is sufficiently strong to cause the valve member to contact the valve-port wall at a position radially outward from the valve-port orifice and thereby prevent passage of fluid through said orifice but said magnetic attraction is low enough to allow disengagement of the valve member from the valve-port wall as a result of a predetermined pressure from weight of urine in a human bladder in fluid communication between the orifice in the valve-port wall and the human bladder.

3. A bladder cycler in accordance with claim 1 wherein:
   the siphon-vent orifice is large enough to allow entry of only a sufficient amount of air to avoid siphon effect of fluid in communication between a terminus of a conveyance and the outlet end of the housing but not large enough to allow passage of a sufficient amount of fluid through the siphon-vent orifice to prevent a suction effect of fluid traveling in a direction of least resistance to a lower elevation through an outlet conveyance attached to the outlet end of the tubular housing.

4. A bladder cycler in accordance with claim 1 and further comprising:
   a fluid conveyance in communication between a siphon-vent orifice positioned at a fluid outlet orifice at the outlet end of the tubular housing and a position outward radially and upstream linearly therefrom.

5. A bladder cycler in accordance with claim 1 and further comprising:
   a selectively small circumferential surface area of the valve-port wall in contact with the magnetic valve member such that magnetic attraction between the wall and the valve member is selectively low as a result of the selectively small surface area of contact and the selectively small surface area of contact of the wall and the valve member allows selectively small area onto which particulates in fluid passing between them can accumulate.

6. A bladder cycler in accordance with claim 1 and further comprising:
   selectively insulative resilient material attached to the surface of the slidable valve member such that magnetic contact between the valve member and the wall is determined selectively thereby and a selectively tight sealing surface is formed between the insulative resilient material and the valve-port wall 7. A bladder cycler in accordance with claim 1 and further comprising:
   an upstream magnetic member positioned at the opposite side of the valve-port wall from the valve member; and
   a valve member comprised of material that is magnetically attractable to the upstream magnetic base member.

8. A bladder cycler in accordance with claim 1 and further comprising:
   an upstream magnetic member positioned at the opposite side of the valve-port wall from the valve member and
   a magnetic valve member with a magnetic pole facing in the direction of an opposite magnetic pole of the upstream magnetic base member.

9. A bladder cycler in accordance with claim 1 and further comprising:
   an upstream magnetic member in slidable contact with portions of the inside periphery of the housing selectively upstream from the valve port wall within the housing;
   a magnetic valve member with a magnetic pole facing in the direction of an opposite magnetic pole of the upstream magnetic member; and
   a resilient member with selective expansion pressure between the upstream magnetic member and the valve-port wall such that the upstream magnetic member is slidable further upstream and magnetic attraction between the two magnetic members is decreased further when the two magnetic members are separated by pressure from fluid mass and tissue resistance within the bladder and resistance to flow of fluid from the bladder during bladder-drainage cycles is minimized.

10. A bladder cycler in accordance with claim 9 and further comprising:
    an upstream abutment positioned selectively upstream from the upstream magnetic member within the housing;
    upstream abutment fluid passageways in communication between the inlet to the housing and fluid passageways at the inside periphery of the housing in fluid communication between the upstream abutment fluid passageways and the upstream side of the valve-port will;
a downstream abutment positioned selectively downstream from the magnetic valve member within the housing; and
downstream abutment fluid passageways in communication between the outlet to the housing and fluid passageways at the inside periphery of the housing in fluid communication between the downstream abutment fluid passageways and the downstream side of the valve-port wall.

11. A bladder cycler in accordance with claim 10 and further comprising:
selectively rounded edges on the upstream magnetic member, the upstream abutment, the upstream fluid passageways, the upstream inlet conveyance, the magnetic valve member, the downstream abutment, the downstream fluid passageways and the downstream outlet conveyance.

12. A bladder cycler in accordance with claim 11 and further comprising:
a sealable insecticide input orifice in the housing upstream from the upstream magnetic member.

13. A bladder cycler in accordance with claim 12 and further comprising:
a fluid conveyance in communication between a siphon-vent orifice positioned at a fluid outlet orifice at the outlet end of the tubular housing and a position outward radially and upstream linearly therefrom.

14. A bladder cycler in accordance with claim 13 wherein:
the siphon-vent orifice is large enough to allow entry of only a sufficient amount of air to avoid siphon effect of fluid in communication between a terminus of a conveyance and the outlet end of the housing but not large enough to allow passage of a sufficient amount of fluid through the siphonvent orifice to prevent a suction effect of fluid traveling in a direction of least resistance to a lower elevation through an outlet conveyance attached to the outlet end of the tubular housing.

15. A bladder cycler in accordance with claim 14 and further comprising:
selectively magnetic insulative resilient material attached to the surface of the slidable valve member such that magnetic contact between the valve member and the wall is determined selectively thereby and a selectively tight sealing surface is formed between the insulative resilient material and the valve-port wall.

16. A bladder cycler in accordance with claim 15 and further comprising:
a selectively small circumferential surface area of the valve-port wall in contact with the magnetic valve member such that the selectively small surface area of contact of the wall and the valve member allows selectively small area onto which particulates in fluid passing between them can accumulate and magnetic attraction between the upstream magnetic member and the magnetic valve member causes the selectively small surface area of the valve-port wall to be pressured into the resilient material for maximized sealing effect.

17. A bladder cycler in accordance with claim 16 and further comprising:
a strainer material attachable to an inlet orifice of the siphon vent conveyance.

18. A bladder cycler in accordance with claim 17 and further comprising:
rounded outside edges of the outside periphery of the housing and the inlet and outlet conveyances such that clothing, linen, human flesh and other materials are not cut and scraped and portions thereof accumulated with infestation effects at the outside surfaces of the bladder cycler.

19. A bladder cycler in accordance with claim 18 and further comprising:
a selectively-swivelable means for attachment of the housing to a leg of a person using the bladder cycler.

20. A bladder cycler in accordance with claim 19 and further comprising:
an outlet conveyance having an outside periphery shaped and sized to be inserted into and held snugly by the inside diameter of medical tubing in fluid communication between the outlet conveyance and a bladder fluid collector; and
an inlet conveyance having an outside periphery shaped and sized to be inserted into and held snugly by the inside diameter of medical tubing in fluid communication between the inlet conveyance and a tubular attachment portion of a bladder drainage tube.

21. A bladder cycler in accordance with claim 1 and further comprising:
a selectively-swivelable means for attachment of the housing to a leg of a person using the bladder cycler.

22. A bladder cycler in accordance with claim 1 and further comprising:
rounded outside edges of the outside periphery of the housing and the inlet and outlet conveyances such that clothing, linen, human flesh and other materials are not cut and scraped and portions thereof accumulated with infestation effects at the outside surfaces of the bladder cycler.

23. A bladder cycler in accordance with claim 1 and further comprising:
an outlet conveyance having an outside periphery shaped and sized to be inserted into and held snugly by the inside diameter of medical tubing in fluid communication between the outlet conveyance and a bladder fluid collector; and
an inlet conveyance having an outside periphery shaped and sized to be inserted into and held snugly by the inside diameter of medical tubing in fluid communication between the inlet conveyance and a tubular attachment portion of a bladder drainage tube.

24. A bladder cycler in accordance with claim 1 and further comprising:
a strainer material attachable to an inlet orifice of the siphon vent conveyance.

25. A bladder cycler in accordance with claim 1 and further comprising:
a sealable insecticide input orifice in the housing upstream from the upstream magnetic member.

26. A bladder cycler in accordance with claim 1 and further comprising:
a downstream abutment positioned selectively downstream from the magnetic valve member within the housing; and
downstream abutment fluid passageways in communication between the outlet to the housing and fluid passageways at the inside periphery of the housing in fluid communication between the downstream abutment fluid passageways and the downstream side of the valve-port wall.

27. A bladder cycler in accordance with claim 1 and further comprising:
an upstream magnetic member in fixed attachment to portions of th inside periphery of the housing at the opposite side of the valve-port wall from the valve member within the housing;
a magnet valve member with a magnetic pole facing in the direction of an opposite magnetic pole of the upstream magnetic base member;
upstream fluid passageways in communication between the inlet to the housing and fluid passageways at the inside periphery of the housing in fluid communication between upstream abutment fluid passageways and the upstream side of the valve-port wall;
a downstream abutment positioned selectively downstream from the magnetic valve member within the housing; and
downstream abutment fluid passageways in communication between the outlet to the housing and fluid passageways at the inside periphery of the housing in fluid communication between the downstream abutment fluid passageways and the downstream side of the valve-port wall.

28. A bladder cycler in accordance with claim 27 and further comprising:
selectively magnetic insulative resilient material attached to the surface of the slidable valve member such that magnetic contact between the valve member and the magnetic member is determined selectively thereby and a selectively tight sealing surface is formed between the insulative resilient material and the valve-port wall.

29. A bladder cycler in accordance with claim 28 and further-comprising:
a selectively small circumferential surface area of the valve-port wall in contact with the magnetic valve member such that the selectively small surface area of contact of the wall and the valve member allows selectively small area onto which particulates in fluid passing between them can accumulate and magnetic attraction between the upstream magnetic member and the magnetic valve member causes the selectively small surface area of the valve-port wall to be pressured into the resilient material for maximized sealing effect.

30. A bladder cycler in accordance with claim 29 and further comprising:
a sealable insecticide input orifice in the housing upstream from the upstream magnetic member.

31. A bladder cycler in accordance with claim 30 and further comprising: a siphon-vent orifice large enough to allow entry of only a sufficient amount of air to avoid siphon effect of fluid in communication between a terminus of a conveyance and the outlet end of the housing but not large enough to allow passage of a sufficient amount of fluid through the siphon-vent orifice to prevent a suction effect of fluid traveling in a direction of least resistance to a lower elevation through an outlet conveyance attached to the outlet end of the tubular housing;
a fluid conveyance in communication between a siphon-vent orifice positioned at a fluid outlet orifice at the outlet end of the tubular housing and a position outward radially and upstream linearly therefrom; and
a strainer material attachable to an inlet orifice of the siphon vent conveyance.

32. A bladder cycler in accordance with claim 31 and further comprising:
selectively rounded edges on the upstream magnetic member, the upstream fluid passageways, the upstream inlet conveyance, the magnetic valve member, the downstream abutment, the downstream fluid passageways and the downstream outlet conveyance; and
rounded outside edges of the outside periphery of the housing and the inlet and outlet conveyances such that clothing, linen, human flesh and other materials are not cut and scraped and portions thereof accumulated with infestation effects at the outside surfaces of the bladder cycler.

33. A bladder cycler in accordance with claim 35 and further comprising:
a selectively-swivelable means for attachment of the housing to a leg of a person using the bladder cycler.

34. A bladder cycler in accordance with claim 33 and further comprising:
an outlet conveyance having an outside periphery shaped and sized to be inserted into and held snugly by the inside diameter of medical tubing in fluid communication between the outlet conveyance and a bladder fluid collector; and
an inlet conveyance having an outside periphery shaped and sized to be inserted into and held snugly by the inside diameter of medical tubing in fluid communication between the inlet conveyance and a tubular attachment portion of a bladder drainage tube.

35. A magnetic bladder cycler comprising:
a non-magnetic tubular housing;
a non-magnetic tubular inlet conveyance positioned concentrically to the axis of an inlet end of the tubular housing;
a non-magnetic tubular outlet conveyance positioned concentrically to the axis of an outlet end of the tubular housing;
a non-magnetic valve-port wall positioned stationary within the tubular housing between the inlet and outlet ends thereof and having a valve orifice linearly concentric to the axis of the tubular housing;
a magnetic valve member having an outside periphery greater than the inside periphery of the valve orifice in slidable contact with the portions of the inside periphery of the housing and positioned between the valve-port wall and the outlet end of the tubular housing;
a magnetic base member selectively positionable linearly to the inside periphery of the housing between the valve-port wall and the inlet conveyance and having a magnetic pole facing an opposite magnetic pole of the magnetic valve member at the opposite side of the non-magnetic valve-port wall;
fluid conveyance means in fluid communication from the inlet conveyance to the valve orifice in the non-magnetic valve-port wall; and
a siphon-vent orifice positioned at the outlet end of the tubular housing.

36. A magnetic bladder cycler according to claim 35 and further comprising:

a siphon-vent orifice large enough to allow entry of only a sufficient amount of air to avoid siphon effect of fluid in communication between a terminus of a conveyance and the outlet end of the housing but not large enough to allow passage of a sufficient amount of fluid through the siphon-vent orifice to prevent a suction effect of fluid traveling in a direction of least resistance to a lower elevation through an outlet conveyance attached to the outlet end of the tubular housing;

a fluid conveyance in communication between a siphon-vent orifice positioned at a fluid outlet orifice at the outlet end of the tubular housing and a position outward radially and upstream linearly therefrom; and a strainer material attachable to an inlet orifice of the siphon vent conveyance.

37. A magnetic bladder cycler according to claim 35 and further comprising:

a sealable insecticide input orifice in the housing upstream from the upstream magnetic member.

38. A magnetic bladder cycler according to claim 35 and further comprising:

a selectively small circumferential surface area of the valve-port wall in contact with the magnetic valve member such that the selectively small surface area of contact of the wall and the valve member allows selectively small area onto which particulates in fluid passing between them can accumulate and magnetic attraction between the upstream magnetic member and the magnetic valve member causes the selectively small surface area of the valve-port wall to be pressured into the resilient material for maximized sealing effect.

39. A magnetic bladder cycler according to claim 35 and further comprising:

selectively magnetic insulative resilient material attached to the surface of the slidable valve member such that magnetic attraction between the valve member and the magnetic member is determined selectively thereby and a selectively tight sealing surface is formed between the insulative resilient material. and the valve-port wall.

40. A magnetic bladder cycler according to claim 35 and further comprising:

a downstream abutment positioned selectively downstream from the magnetic valve member within the housing; and downstream abutment fluid passageways in communication between the outlet to the housing and fluid passageways at the inside periphery of the housing in fluid communication between the downstream abutment fluid passageways and the downstream side of the valve-port wall.

41. A magnetic bladder cycler according to claim 35 and further comprising:

a selectively-swivelable means for attachment of the housing to a leg of a person using the bladder cycler.

42. A magnetic bladder cycler according to claim 35 and further comprising:

an outlet conveyance having an outside periphery shaped and sized to be inserted into and held snugly by the inside diameter of medical tubing in fluid communication between the outlet conveyance and a bladder fluid collector; and an inlet conveyance having an outside periphery shaped and sized to be inserted into and held snugly by the inside diameter of medical tubing in fluid communication between the inlet conveyance and a tubular attachment portion of a bladder drainage tube.

43. A magnetic bladder cycler according to claim 35 and further comprising:

selectively rounded edges on the magnetic valve member, the downstream abutment, the downstream fluid passageways and the downstream outlet conveyance; and rounded outside edges of the outside periphery of the housing and the inlet and outlet conveyances such that clothing, linen, human flesh and other materials are not cut and scraped and portions thereof accumulated with infestation effects at the outside surfaces of the bladder cycler.

44. A magnetic bladder cycler according to claim 35 and further comprising:

a tubular member in fluid communication between the inlet conveyance and the valve orifice in the valve-port wall; and a bearing orifice in the magnetic base member in slidable contact with the outside periphery of the tubular member.

45. A magnetic bladder cycler according to claim 47 and further comprising:

an offset cam member in swivelable relationship to the housing and in cam-follower relationship to a cam follower on the magnetic base member.

46. A magnetic bladder cycler according to claim 35 and further comprising:

a tubular member in fluid communication between the inlet conveyance and the valve orifice in the valve-port wall;

a bearing orifice in the magnetic base member in slidable contact with the outside periphery of the tubular member;

an adjustment bolt in threaded relationship to the magnetic base member;

an adjustment-bolt aperture linear to the tubular member in the wall of the housing; and a hand-turnable adjustment-bolt head extended through the adjustment-bolt aperture from the magnetic base member.

47. A magnetic bladder cycler according to claim 35 and further comprising:

a tubular member in fluid communication between the inlet conveyance and the valve orifice in the valve-port wall;

a bearing orifice in the magnetic base member in slidable contact with the outside periphery of the tubular member;

an adjustment-spring aperture at opposite sides of the housing;

a circumferential adjustment resilient member in contact with both sides of the magnetic base member and having outward resiliency pressure against the inside periphery of the housing; and an adjustment handle extended through an adjustment handle orifice in the housing in pressure-resistance relationship to the resilient member.

48. A magnetic bladder cycler according to claim 38 wherein the magnetic base member is rigidly positionable linearly to the inside periphery of the housing between the valve-port wall and the inlet conveyance at a distance upstream from the valve-port wall selected in relationship to the magnetic attraction of the magnetic valve member and the magnetic base member to each other.

49. A method for using a magnetic bladder cycler consisting of: an non-magnetic tubular housing; a non-magnetic tubular inlet conveyance positioned concentrically to the axis of an inlet end of the tubular housing; an non-magnetic tubular outlet conveyance positioned concentrically to the axis of an outlet end of the tubular housing; a valve-port wall positioned stationary within the tubular housing between the inlet and outlet ends thereof and having a valve orifice linear to the axis of the tubular housing; a magnetic base member rigidly positionable linearly to the inside periphery of the housing between the valve-port wall and the inlet conveyance at a distance upstream from the valve-port wall selected in relationship to magnetic attraction of a magnetic valve member and the magnetic base member to each other; a magnetic valve member having magnetic attraction to the magnetic base member at the opposite side of the valve-port wall and having an outside periphery greater than the inside periphery of the valve orifice in slidable contact with portions of the inside periphery of the housing and positioned between the valve-port wall and the outlet end of the tubular housing; a fluid conveyance means in fluid communication from the inlet conveyance to the valve orifice in the non-magnetic valve-port wall; fluid conveyance means in fluid communication from the valve orifice in the non-magnetic valve-port wall to the outlet conveyance; and a siphon-vent orifice positioned at the outlet end of the tubular housing; and comprising:

selection of a magnetic bladder cycler with predetermined valve opening resistance between the valve member and the base member on the basis of the size and tissue condition of the bladder of a person on whom the cycler is to be used;

attaching the inlet conveyance to a tubular attachment end of a bladder drainage tube;

attaching the outlet conveyance to a tubular conveyance from the bladder cycler to a bladder discharge receptacle;

attaching the cycler to a leg of a person using the bladder cycler;

inserting a bladder-entry end of a bladder drainage tube through the uretha and selectively into the bladder of a person using the bladder cycler;

positioning the magnetic bladder cycler to approximately a 45-degree angle of the outlet conveyance down from a horizontal position of the leg;

positioning of the tube attached to the outlet conveyance at a downwardly slanting angle from the bladder cycler to a bladder discharge receptacle; and allowing the bladder to discharge cyclically into the bladder discharge receptacle from either a vertical or a horizontal position of the leg to which it is attached.

50. A method of using a magnetic bladder cycler consisting of: a non-magnetic tubular housing; a non-magnetic tubular inlet conveyance positioned concentrically to the axis of an inlet end of the tubular housing; a non-magnetic tubular outlet conveyance positioned concentrically to the axis of an outlet end of the tubular housing; a non-magnetic valve-port wall positioned stationary within the tubular housing between the inlet and outlet ends thereof and having a valve orifice concentric to the axis of the tubular housing; a magnetic valve member having an outside periphery greater than the inside periphery of the valve orifice in slidable contact with the portions of the inside periphery of the housing and positioned between the valve-port wall and the outlet end of the tubular housing; a magnetic base member selectively positionable linearly to the inside periphery of the housing between the valve-port wall and the inlet conveyance and having a magnetic pole facing an opposite magnetic pole of the magnetic valve member at the opposite side of the non-magnetic valve-port wall; fluid conveyance means in fluid communication from the inlet conveyance to the valve orifice in the non-magnetic valve-port wall; a siphon-vent orifice positioned at the outlet end of the tubular housing; and a selectively swivelable means for attachment of the housing to a leg of a person using the bladder cycler; and comprising:

attaching the inlet conveyance to a tubular attachment end of a bladder drainage tube;

attaching the outlet conveyance to a tubular conveyance from the bladder cycler to a bladder discharge receptacle;

attaching the selectively swivelable means to a leg of a person using the bladder cycler;

inserting bladder-entry end of a bladder drainage tube through the urethra and selectively into the bladder of a person using the bladder cycler;

swiveling the magnetic bladder cycler to approximately a 45-degree angle of the outlet conveyance down from a horizontal position of the leg;

positioning of the tube attached to the outlet conveyance at a downwardly slanting angle from the bladder cycler to the bladder discharge receptacle;

varying the opening pressure of the magnetic valve member to a level suited to the bladder fullness comfort level of the individual by positioning the magnetic base member in the direction of the inlet conveyance for ease of opening and in the direction of the outlet conveyance for increase in pressure required for opening the valve;

varying the opening pressure of the magnetic valve member by positioning the magnetic base member in the direction of the outlet conveyance when desired for delaying discharge for any desired reason;

varying the opening pressure of the magnetic valve member by positioning the magnetic base member in the direction of the inlet conveyance when desired for expediting discharge for any desired reason;

allowing the bladder to discharge cyclically into the bladder discharge receptacle from either a vertical or a horizontal position of the leg to which it is attached; and positioning the magnetic base member to extreme end of travel in the direction of the inlet conveyance after bladder discharge as desired to assure full drainage of the bladder.

* * * * *